(12) United States Patent
Seibt

(10) Patent No.: US 10,940,811 B2
(45) Date of Patent: Mar. 9, 2021

(54) HAND HYGIENE ARRANGEMENT

(71) Applicant: Airbus Operations GmbH, Hamburg (DE)

(72) Inventor: Christian Seibt, Hamburg (DE)

(73) Assignee: Airbus Operations GmbH

( * ) Notice: Subject to any disclaimer, the term of this patent is extended or adjusted under 35 U.S.C. 154(b) by 0 days.

(21) Appl. No.: 15/609,241

(22) Filed: May 31, 2017

(65) Prior Publication Data

US 2017/0341602 A1 Nov. 30, 2017

(30) Foreign Application Priority Data

May 31, 2016 (DE) .................... 10 2016 110 061.7

(51) Int. Cl.
| | |
|---|---|
| *B60R 15/02* | (2006.01) |
| *A47K 1/04* | (2006.01) |
| *A47K 10/48* | (2006.01) |
| *A61L 2/26* | (2006.01) |

(52) U.S. Cl.
CPC ............... *B60R 15/02* (2013.01); *A47K 1/04* (2013.01); *A47K 10/48* (2013.01); *A47K 2210/00* (2013.01); *A61L 2/26* (2013.01)

(58) Field of Classification Search
CPC .................................. B60R 15/02; A47K 1/04
USPC ..................................................... 4/625, 638
See application file for complete search history.

(56) References Cited

U.S. PATENT DOCUMENTS

| | | | |
|---|---|---|---|
| 4,398,310 A | 8/1983 | Lienhard | |
| 4,865,631 A | 9/1989 | Stroby et al. | |
| 5,372,718 A * | 12/1994 | Zebian | B01D 29/117 |
| | | | 210/301 |
| 5,727,579 A * | 3/1998 | Chardack | A47K 10/485 |
| | | | 134/102.3 |
| 5,992,430 A * | 11/1999 | Chardack | A47K 10/46 |
| | | | 134/102.3 |
| 9,139,302 B2 | 9/2015 | Dehn et al. | |
| 2012/0186011 A1 | 7/2012 | Wright et al. | |

(Continued)

FOREIGN PATENT DOCUMENTS

| | | |
|---|---|---|
| DE | 697 04 768 T2 | 10/2001 |
| DE | 10 2011 010 913 A1 | 8/2012 |

(Continued)

*Primary Examiner* — Lauren A Crane
(74) *Attorney, Agent, or Firm* — Lerner, David, Littenberg, Krumholz & Mentlik, LLP

(57) ABSTRACT

A hand hygiene on board of a vehicle includes a washing device including a water supply device, a basin device with a hand receiving device and a water collecting region with a discharge opening, and a drying device including an air discharge device for generating an air stream in the hand receiving region The air discharge device is connected to the hand receiving region and a negative pressure device connected to the air discharge device. The stream of air for the hand drying process is generatable by the negative pressure device. The air discharge device is connected to the discharge opening of the basin device such that air and fluids are discharged via the discharge opening, which forms a common disposal opening. The negative pressure device is additionally designed for suctioning solids thrown into the water collecting region, besides fluids, for disposal over the common disposal opening.

18 Claims, 5 Drawing Sheets

(56) References Cited

U.S. PATENT DOCUMENTS

2012/0210509 A1* 8/2012 Dehn ..................... B64D 11/02
                                                         4/638
2015/0059085 A1* 3/2015 Seibt ..................... A47K 10/48
                                                         4/638
2015/0060338 A1   3/2015 Burd

FOREIGN PATENT DOCUMENTS

WO         80/01983 A1   10/1980
WO      2014/078640 A2    5/2014

* cited by examiner

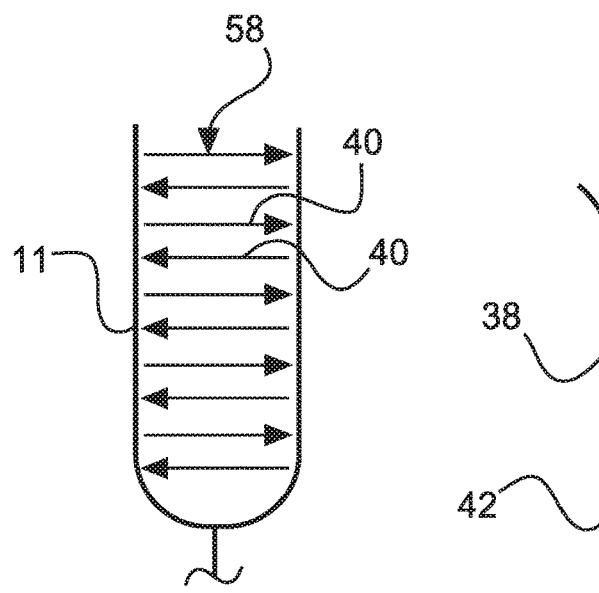
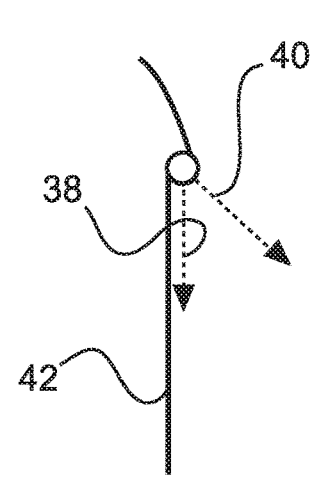
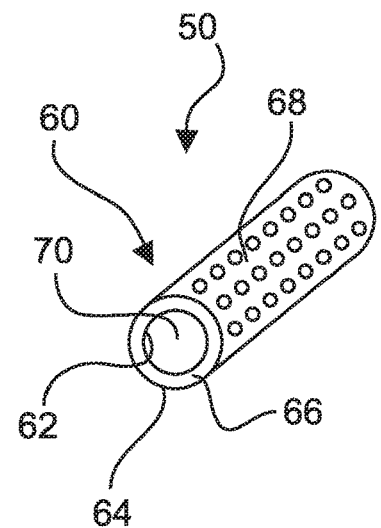
Fig. 3    Fig. 4    Fig. 5
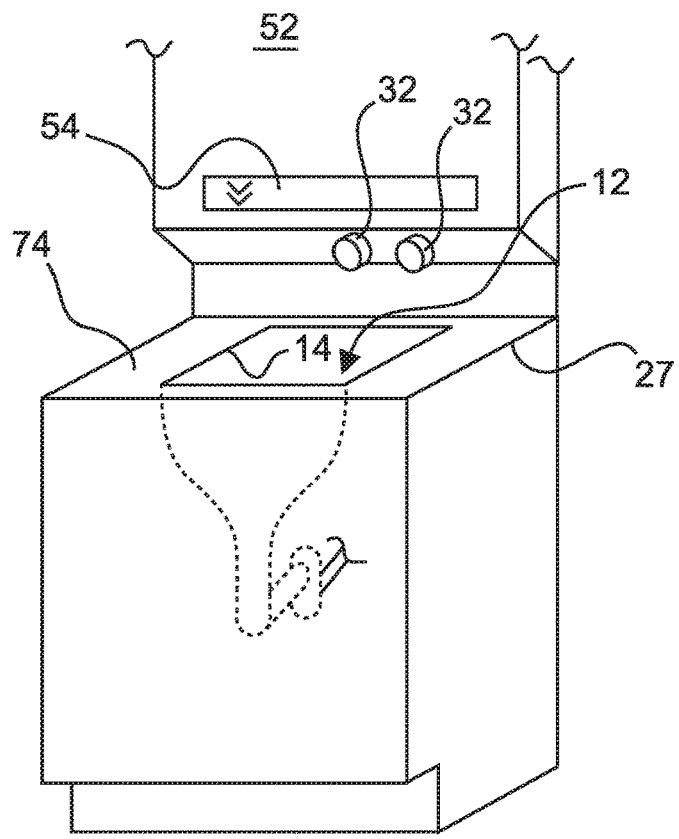
Fig. 6

HAND HYGIENE ARRANGEMENT

FIELD OF THE INVENTION

The present invention addresses hand hygiene on board a vehicle and particularly addresses a hand hygiene arrangement for a sanitary module for a vehicle, a galley module for an aircraft, an aircraft and a method for hand hygiene on board a vehicle

BACKGROUND OF THE INVENTION

On board of vehicles, for example aircraft, as e.g. passenger aircraft, hand washbasins are provided in order to enable passengers or vehicle personnel to wash their hands. For example, hand washbasins are provided in conjunction with lavatories on board of vehicles or in conjunction with galleys. DE 10 2011 010 913 A1 for example describes a hand drying device for an aircraft, which is integrated into a washbasin, such that the hand washing and hand drying process can be conducted within the washbasin of the washstand. However, it became apparent that passengers and personnel increasingly have higher demands to operating and use of sanitary devices.

BRIEF SUMMARY OF THE INVENTION

An aspect of the present invention may therefore lie in further increasing the user comfort.

The aspects described in the following are also valid for the hand hygiene arrangement, the sanitary module, the galley module, the aircraft and the method for hand hygiene on board a vehicle.

According to an embodiment of the invention, a hand hygiene arrangement for the use on board a vehicle is provided. The hand hygiene arrangement comprises a washing device, a basin device and a drying device. The washing device comprises a water supply device for a hand washing process. The drying device comprises an air discharge device for a hand drying process, in order to create a stream of air for the hand drying process. A hand receiving region is provided and the stream of air is creatable in the hand receiving region, i.e. it may be created there. The air discharge device is connected to the hand receiving region and a negative pressure device is provided which is connected to the air discharge device; and by means of the negative pressure device, the stream of air for the hand drying process is creatable, i.e. it may be created there. The basin device comprises the hand receiving region and a water collecting region that is provided with a discharge opening. The air discharge device is connected to the discharge opening of the basin device such that air and fluids are discharged via the discharge opening, which forms a common disposal opening. The negative pressure device is additionally designed for suctioning solids that are thrown into the water collecting region besides fluids for disposal over the common disposal opening.

By this, a user is able to use the drying device after washing the hands on the one hand, at which a stream of air for drying the hands is provided. On the other hand, the user may also access e.g. paper towels, so as to dry the hands or the face therewith. The possibility to dispose solid materials that are thrown into the water collecting region offers the user further comfort as the user does not need to look for a separate collecting bin. The contact with edge regions of a waste insertion bin is prevented. Also, the necessity for emptying of waste bins is reduced, as exemplarily paper towels may be disposed over the hand hygiene arrangement and do not necessarily have to be inserted into a waste bin, which is exemplarily provided in a lavatory.

According to an example, the negative pressure device is designed for suctioning paper towels thrown into the basin device for disposal over the common disposal opening.

In an example, the common disposal opening is provided as a single opening, and thus as the only opening for disposing of water, air and paper towels.

Thus, the same mechanism is used for different purposes, which reduces further effort and besides a weight reduction also involves reduced installation space.

Hence, for discharge, a common suction of waste water and paper hand towels is provided by the common disposal opening, i.e. by the discharge opening. The discharge opening provides a common negative pressure connection for discharge of air, water and paper towels. The same negative pressure connection is used for suction and thus disposal of waste water, for example resulting from a hand or face washing process, and of paper towels resulting from a hand or face drying process, which can be referred to as a "manual" drying process, since the towels are manually handled. In addition, the same negative pressure connection is also used for generating the stream of air for the hand drying process, which can be referred to as a "mechanical" drying process, since the air stream is mechanically generated.

According to an example, downstream of the common disposal opening, a separator device for the separation of solids and fluids is provided.

This furthermore results in that a separation of solids and fluids may be conducted already on board, so as to e.g. dispose of solids and fluids independent from each other if necessary. By this, different amounts of material to be disposed of may be discharged better and stored for the flight time.

According to an example, the separator device is a double-walled pipeline. Between an inner pipe, which is connected to the common disposal opening, and an outer pipe an intermediate space is provided. The inner pipe comprises a plurality of holes and an inner space created by the inner tube is connected to the intermediate space through the plurality of holes.

According to an example, the separator device comprises at least one directional change along the flow direction in form of a band, in order to exert a centrifugal force on the mixture that flows through, with which fluid(s) contained in the mixture may enter the intermediate space through the openings in order to be dischargeable separately, i.e. to be discharged.

According to an example, the hand receiving region comprises a hand receiving opening, which is designed as an air supply device. With the negative pressure device, a negative pressure may be created at the air discharge device, i.e. it is creatable, such that ambient air may be suctioned in through the hand receiving opening and the stream of air may be created in the hand receiving region for drying hands.

According to an example, the washing device comprises a water discharge device. The discharged water is conducted over the basin device and the common disposal opening to the water discharge device.

According to an example, the negative pressure device is connected to the common disposal opening in order to dispose of the collected water and solids and to generate the stream of air.

According to an example, the basin device is designed having a circumferential water spray device at least partially in its upper edge region as a secondary water supply for spraying water from the edge region into the center of the basin device in form of a plurality of spray jets.

According to an embodiment of the invention, also a sanitary module for a vehicle is provided. The sanitary module comprises at least one sanitary function element from the group of toilet, bidet, shower, washbasin and diaper changing table. Hereby, a hand hygiene arrangement is provided according to one of the previously described examples.

According to an embodiment of the invention, also a galley module for an aircraft is provided. The galley module comprises at least one galley function element from the group of food storage, food processing, food preparing and food disposal. Hereby, a hand hygiene arrangement according to one of the previously described examples is provided.

According to an embodiment of the invention, also an aircraft is provided, which comprises a fuselage construction and a cabin space. In the cabin space, at least one sanitary module according to the previously mentioned example and/or at least one galley module according to the previously described example is provided.

According to an aspect of the invention, also a method for hand hygiene on board a vehicle is provided. The method comprises the following steps:

In a first step, also denoted as step a), at least one wet hand is arranged in a hand receiving region of a basin device.

In a second step, also denoted as step b), a negative pressure is generated at a disposal opening of the basin device, through which a stream of air in the hand receiving region is generated.

In a third step, also denoted as step c), the hand is dried in the stream of air is provided.

In a fourth step, also denoted as step d), a paper towel thrown into the hand receiving region is disposed through the stream of air.

The negative pressure is also used for disposing of water and paper towels via the disposal opening, which forms a common disposal opening.

According to an example, prior to step a), the following step sequence is provided:

Initially, in a step, which is also denoted as step i), a water jet is created and at least one hand is arranged in the water jet in order to wash the hand; and in a further step, which is also denoted as step ii), a hand to be dried is washed, wherein the water is collected and discharged in a water collecting region of the basin device, and wherein the water collecting region comprises the disposal opening.

According to an aspect of the invention, it is provided that with a device for washing the hands also a drying process is enabled with the same device plus a disposal option for paper towels. Washing and drying and paper towel disposal are offered with the same device, e.g. subsequently in a timely offset manner.

For creating the stream of air for drying hands, a negative pressure is provided, which suctions air from the region, in which the hands may be arranged for drying. By this, the stream of air is generated, which leads to drying the hand. It is also provided that the washbasin, which is also used for drying the hands by holding the hands in this region, is also designed as collection and disposal device for e.g. paper towels. The paper towels may thereby be disposed over the same opening as exemplarily the water or the suctioned air.

It is to be noted that the features of the exemplary embodiments of the devices are also valid for embodiments of the methods and vice versa. Furthermore, also those features may be freely combined at which this is not explicitly mentioned.

These and further aspects of the invention are apparent with reference to the following explanations.

BRIEF DESCRIPTION OF THE DRAWINGS

In the following, exemplary embodiments of the invention are discussed on the basis of the attached drawings. It is shown:

FIG. 3 an example for a detail of the water supply of a hand hygiene arrangement;

FIG. 4 a schematic vertical section for a detail for water supply;

FIG. 5 an example for a separator device;

FIG. 6 a perspective view of a further example of a hand hygiene arrangement;

DETAILED DESCRIPTION

Figure 1:
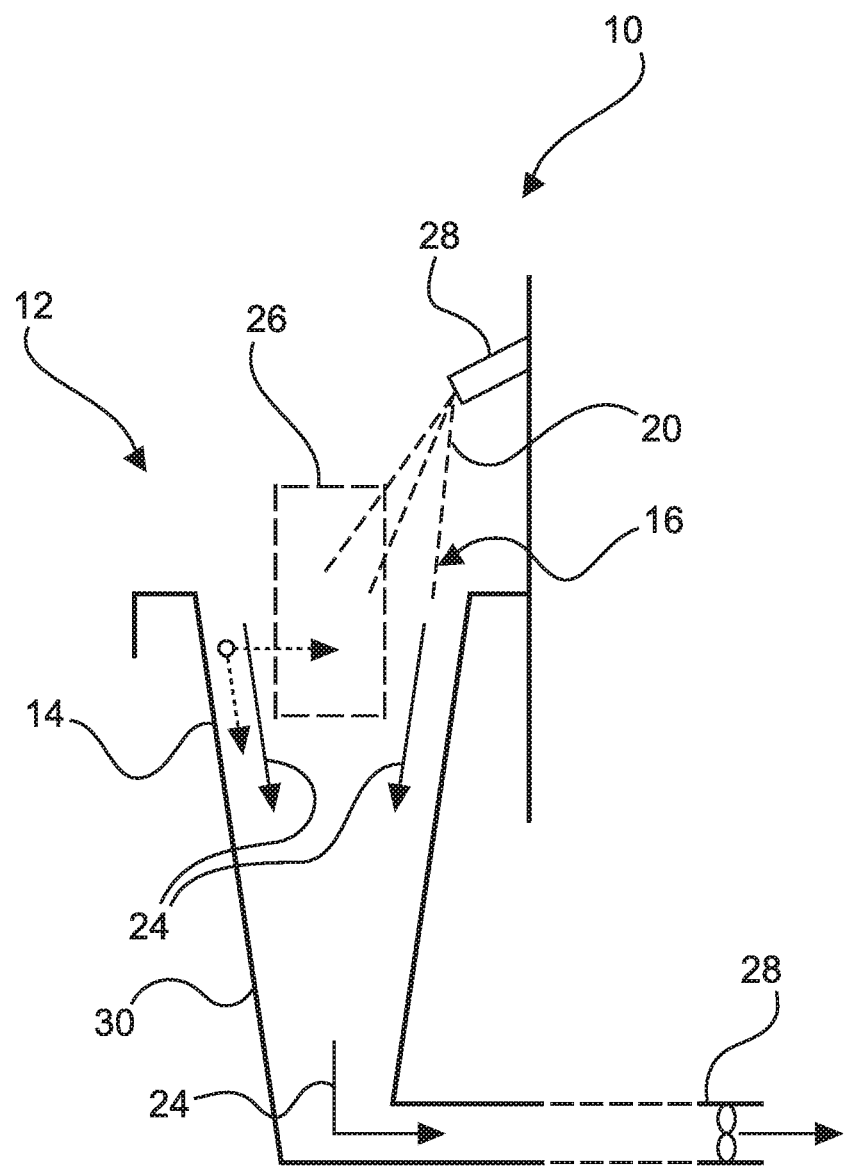
FIG. 1 an example for a hand hygiene arrangement for the use on board of a vehicle.

FIG. 1 shows a hand hygiene arrangement 10 for the use on board of a vehicle, exemplarily on board of an aircraft, as exemplarily an aeroplane, e.g. a passenger aircraft, or also on board of a rail vehicle, i.e. a train; or also for the use on board of a bus. The hand hygiene arrangement 10 comprises a washing device 12, a basin device 14 and a drying device 16. The washing device 12 comprises a water supply device 18 for a hand washing process. The water supply is schematically indicated by means of dashed lines 20. The drying device 16 comprises an air discharge device 22 for creation of a stream of air, indicated with arrows 24, for a hand drying process. Also, a hand receiving region 26 is provided, which is indicated by means of a dashed rectangle. The stream of air is creatable in the hand receiving region 26. The air discharge device 22 is connected to the hand receiving region 26 and a negative pressure device 28 is provided, which is connected to the air discharge device and schematically indicated with a propeller of a fan, wherein by means of the negative pressure device, the stream of air for the hand drying process may be generated. The negative pressure device 28 may be an active element, such as a fan, or it may exploit a present pressure difference, exemplarily between a cabin inner space and an outer space, if there is a sufficiently low pressure. The water and optionally the solids are of course not disposed overboard.

The basin device 14 comprises the hand receiving region 26 and a water collecting region 30 that is provided with a discharge opening (e.g. in the region where the arrow 24 is shown). The air discharge device 22 is connected to the discharge opening of the basin device 14 such that air and fluids are discharged via the discharge opening, which forms a common disposal opening. Besides fluids, the negative pressure device is additionally designed to suction solids that are thrown into the water collecting region 30 for disposal over the common disposal opening.

According to an option, the negative pressure device is designed for suctioning paper towels thrown into the basin device for disposal through the common disposal opening.

The term "paper towel" exemplarily refers to paper towels, as well as cleansing tissues, handkerchiefs and other sanitary articles thrown into the basin.

The "hand receiving region" may also be referred to as hand treatment region. The hand receiving region is a volume partially enclosed by the basin device, which is designed for receiving the hand or the hands of the user.

The "hand hygiene arrangement" may also be referred to as hand cleaning arrangement. Hand cleaning primarily refers to drying the hands and washing the hands. It may also be provided a disinfection by means of a disinfection agent applied onto the hands, which is e.g. dripped, sprinkled or sprayed on.

The negative pressure device is designed as a vacuum suctioning device. Hence, the negative pressure device is provided for two purposes, i.e. on the one hand for creating a stream of air and on the other hand for suctioning exemplarily water and solids.

In an example, it is provided that the negative pressure device creates a permanent basic air current (standby air current).

For example, the stream of air comprises a first and a second air stream intensity. The term "air stream intensity" refers to the amount of air (air volume) and velocity in relation to the time. The first air stream intensity is provided e.g. for suctioning water and the second air stream intensity is provided for drying of hands. The second air stream intensity thereby is exemplarily greater than the first air stream intensity.

In an example, the water supply device comprises a primary water supply above the basin device, exemplarily through an indicated water tap, with which a water jet in the direction of the basin device may be created. The water jet may be composed of a plurality of water spray jets.

In an example, it is provided that the negative pressure device is additionally designed for suctioning water collected in the water collecting region for disposal over the disposal opening.

For example, the negative pressure device is designed for suctioning paper towels thrown into the water collecting region for disposal over the disposal opening.

In an example, the water collecting region and the hand receiving region are designed as a bi-functional receiving region. The hand receiving region and the water collecting region are exemplarily designed integrally. For example, the hand receiving region is created by the water collecting region. In another example, the water collecting region is created by the hand receiving region.

In an example, the washing device comprises a water discharge device. The discharged water is conducted through the basin device and the common disposal opening to the water discharge device. The water discharge device is thus connected to the water collecting region. The water discharge device is hence created by the air discharge device.

In an example, a solids disposal device is connected to the water collecting region and/or the hand receiving region. The solids disposal device is exemplarily created by the air discharge device.

Figure 2:
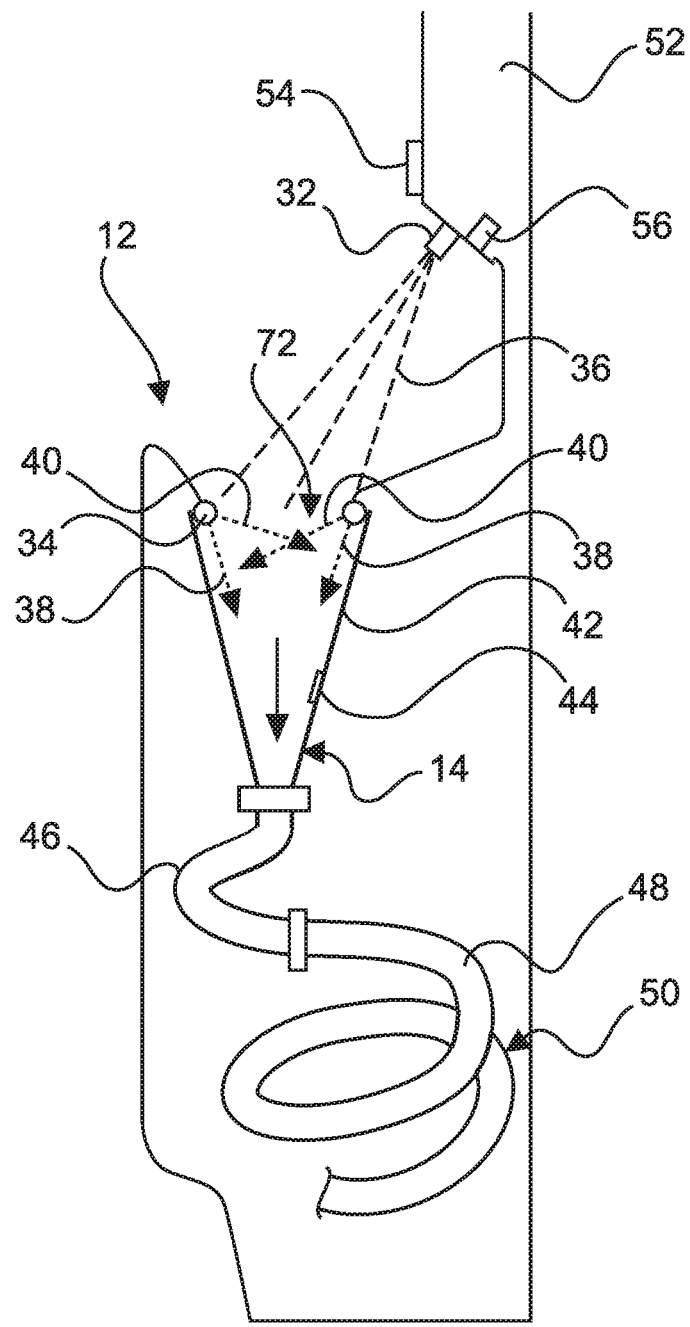
FIG. 2 a further example of a hand hygiene arrangement.

In FIG. 2, a further example of a hand hygiene arrangement is shown in a schematic vertical section. The washing device 12 comprises a primary spray nozzle 32 arranged above it as well as a secondary spray unit 34. The spray nozzle 32 exemplarily creates a bundle of water jets 36. The spray unit 34 may exemplarily create spray jets 38 directed downwardly, which are also referred to as tangential fluid jets. Hereby, also fluid jets 40 may be created, which intersect each other.

As an option, at least one sensor is provided, exemplarily a first sensor 42 and a second sensor 44. The first sensor 42 may exemplarily be provided for detecting a hand arranged in front of it in order to activate the drying process. The second sensor 44 may exemplarily be provided for personnel protection and may be designed for stopping the installation when reaching into this region.

In an option, it is provided that the suctioned air volume flow for creation of the stream of air for the hand drying process is adapted depending on the insertion depth of the hand into the receiving opening. For example, the air volume flow may be reduced if the hand is inserted further into a tapering receiving opening or further extends inside, respectively.

At a lower end of the basin device 14, exemplarily a first pipe segment 46 is connected, in which a maintenance and revision unit (not shown in detail) may be provided. Connecting thereto, a pipe segment 48 is provided, which comprises a spiral course.

Downstream of the pipe segment 46, for example a valve may be provided, which controls the air volume flow. The valve may also be provided above the pipe segment 46.

In a further option, it is provided that a sensor may detect a paper towel being thrown into the basin opening and that is to be suctioned at a lower end. Then, a temporary increase of the air volume flow may be conducted. The sensor differentiates between a paper towel and a hand.

For example, downstream of the common disposal opening, a separator device 50 is provided for separating solids and fluids.

The valve may also be provided downstream of the separator device 50.

When arranging the hygiene arrangement exemplarily in a sanitary module, a mirror cabinet 52 may be provided above it, in which exemplarily also an activation and information panel 54 is provided as well as a further, i.e. a third, sensor 56, with which exemplarily the spray nozzle 32 may be activated.

FIG. 3 schematically shows a horizontal section through a hand receiving region and exemplarily shows fluid jets 58, which intersect each other.

In a cutout view, FIG. 4 shows an edge detail with the water supply device 34, which creates the fluid jet 40 that intersects and the further water jet 38 designed as a tangential jet.

FIG. 5 shows an example for the separator device 50. The separator device 50 is designed as a double-walled pipeline 60. Between an inner pipe 62, which is connected to the common disposal opening, and an outer pipe 64, an intermediate space 66 is provided. The inner pipe comprises a plurality of holes 68, and an inner space 70 created by the inner pipe 62 is connected to the intermediate space 66 through the plurality of holes 68. The outer pipe 64 is designed so as to be closed.

As a further option, it may be provided that the separator device 50 comprises at least one directional change in form of a curvature in flow direction in order to create a centrifugal force if flown through by a mixture, with which fluid contained in the mixture reaches the intermediate space through the openings in order to be disposed of separately.

For example, paper towels in the basin device may be disposed of and separately led away through the separator device. The separator device may also be referred to as separator or liquid separator.

In an example, the curvature is a spiral shaped drain line, as indicated in FIG. 2. In another example, the curvature is designed as a meandering strap.

As an option, it is shown in FIG. 2 that the hand receiving region may be designed as a hand receiving opening 72, which is designed as an air supply device. Through the negative pressure device, a negative pressure may be generated at the air discharge device, such that ambient air may be suctioned through the hand receiving opening and that the stream of air is generated in the hand receiving region for drying of hands.

In an example, the hand cleaning device is a bi-functional hand hygiene device for washing of hands and drying of hands, further increasing user comfort by enabling a disposal of paper hand towels via common disposal opening of the wash basin.

The stream of air created for the hand drying is generated from ambient air, which is exemplarily suctioned by a suction device. Since the suction is conducted over a chamber, in the chamber a stream of air arises, in which hands may be dried.

The negative pressure device may also be realized as negative pressure generation device.

The basin device comprises a drain in order to dispose of the collected water. In an example, the water collecting region is connected to the drain in a fluid technical manner.

In an example, it is provided that the washing device comprises a water discharge device. The discharged water is conducted through the basin device and the common disposal opening to the water discharge device.

In a further example, the negative pressure device is connected to the common disposal opening in order to dispose of the collected water and solids and to generate the stream of air.

The basin device exemplarily comprises an upper, widened region, which is designed as the water collecting region and which is provided as hand washing region. The basin device also has a lower, more narrow region, which is designed as hand receiving region, wherein the disposal opening is arranged at the lower end of the more narrow region.

In a further example, it is provided that the basin device in its upper edge region (as already explained above) is designed to at least partially comprise a circumferential water spray device as secondary water supply, in order to spray water in form of a plurality of spray jets into the middle of the basin device.

It is possible to create a water film, which is directed downwardly, at least partially at the inner walling of the basin device through the downwardly oriented tangential fluid jets.

In an example, not shown in detail, a sanitary module for a vehicle is provided, which comprises at least one sanitary function element from the group of toilet, bidet, shower, washbasin and diaper changing table. Also, a hand hygiene arrangement according to one of the previous examples is provided.

The sanitary module for an aircraft may also be designed as an aircraft sanitary module and is also referred to as a lavatory unit.

In a further example, which is not shown, too, a galley module for an aircraft is provided, which comprises at least one galley function element from the group of food storage, food processing, food preparation and food disposal. Also, a hand hygiene arrangement according to one of the above described examples is provided.

The term "food" exemplarily refers to meals and beverages, which are primarily intended for consumption on board of the aircraft. The term "galley function element" refers to devices provided in galleys, which are intended for serving the passengers with beverages and meals during their stay on board of an aircraft. The term "food storage" refers to technical devices, which serve for stowage or storing, respectively, and transportation of beverages and meals. For example, cooled and uncooled storage regions may be provided. The term "food processing" refers to technical devices, which are provided for processing already prepared meals and beverages for the use, e.g. for warming and heating, or also for cooling, for example heating ovens, microwave ovens and cooling regions. The term "food preparing" refers to technical devices, which are provided for preparing meals and beverages, e.g. sandwiches, salad or fruits and other fresh products, or to make tea or coffee. The term "food disposal" refers to the disposal of leftovers and waste, which accumulate in conjunction with the supply on board, for example waste bins.

The vehicle may e.g. be an aircraft, in particular an aeroplane.

The vehicle may also be e.g. a watercraft, a rail craft or a road craft, e.g. a passenger ship, a train or a bus. In an example, an underwater craft is provided. In another example, a spacecraft is provided.

In FIG. 6, a perspective view of a further example of the hand hygiene arrangement 10 is shown. The washing device 12 with the basin device 14 is exemplarily arranged in a wash table 74. Above the wash table, exemplarily the previously mentioned mirror cabinet 52 is placed.

Figure 7:
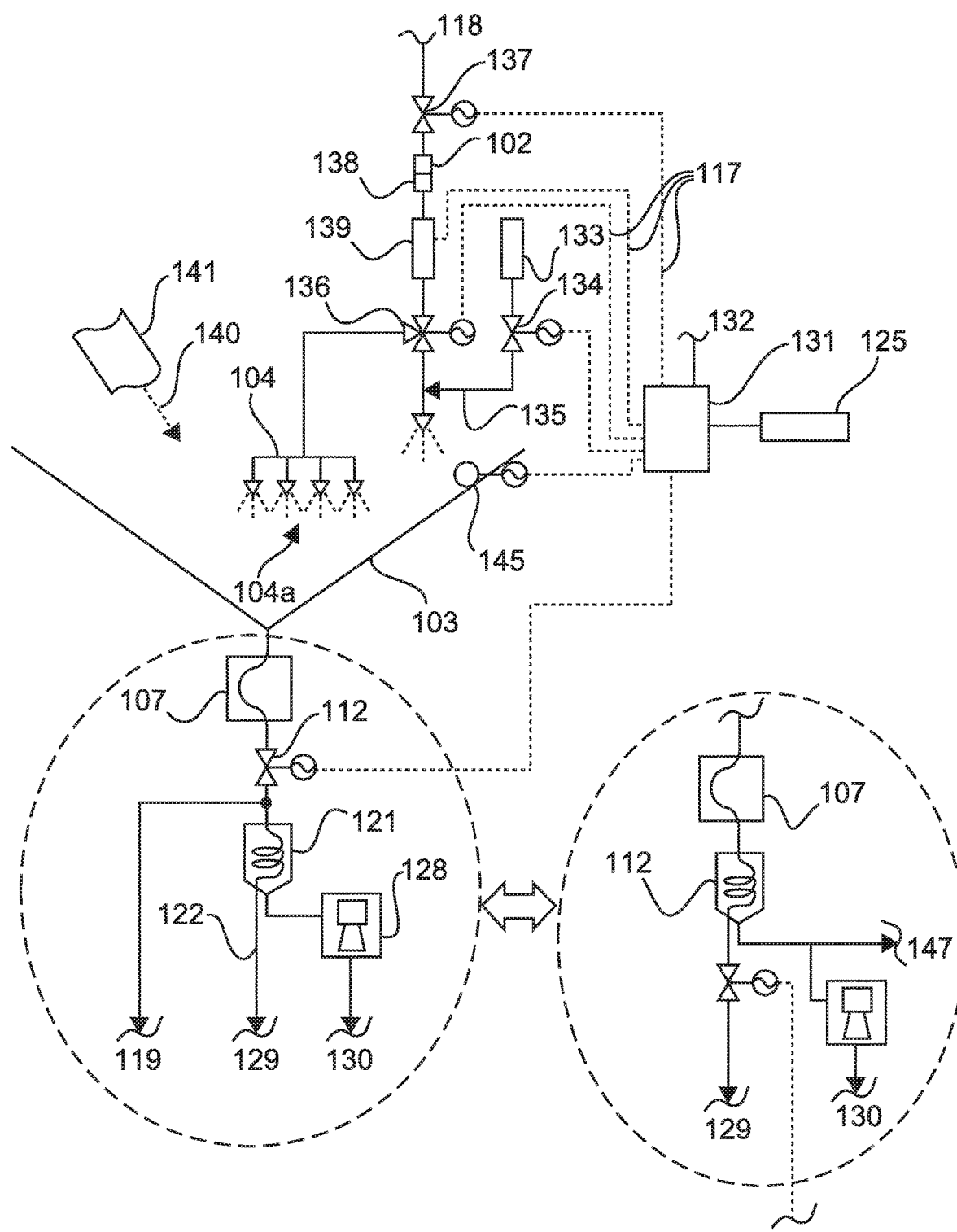
FIG. 7 an example for a functional diagram of a hand hygiene arrangement.

In FIG. 7, a functional diagram is shown. A disposal and suctioning device 103 is schematically indicated as a collecting funnel and serves for the drying of hands and the paper towel disposal. Nearby, a spray unit 104 is provided, which comprises a plurality of spray nozzles 104a. Also, a spray nozzle 101 is provided, which is connected to the three-way control valve through a connection. For this exemplarily in a storage receptacle 133, a disinfection means, soap, etc. may be stored, in order to supply these through a control valve 134 on demand and by means of a secondary line supply it to the spray nozzle. The spray unit 104 is connected to a three-way control valve 136, which in turn is connected a water heating device 139. After that, a check valve 138 as well as a drainage valve with a check valve 102 before a further control valve 137 is provided. A freshwater connection 118 may be provided connected thereto. A connection to a control unit 131 is indicated by means of dashed lines 117 that comprises a power supply 132 or is connected thereto. An activation and information panel 125 is connected to the control unit 131.

As an option, a disinfection and illumination unit 145 is provided, e.g. a UV disinfection device (UV=ultraviolet light).

An insertion of a paper towel 141 is indicated by means of an arrow 140.

A maintenance and revision unit 107 is exemplarily connected to the disposal and suctioning device 103, followed by a flushing valve 112 controlled by the control unit 131. The flushing valve 112 in turn is exemplarily connected to a vacuum port 119, or with a further vacuum port 129 through the separator or also to a grey water port 130 through a drainage valve 128 with. Also, with this alternative, a vacuum port 122 may be provided.

The separator unit having a casing pipe and an inner pipe is schematically indicated by means of a spiral.

In a further option, it is shown that besides a connection to a grey water port 147, also the connection to a further grey water port 130 may be provided.

Figure 8:
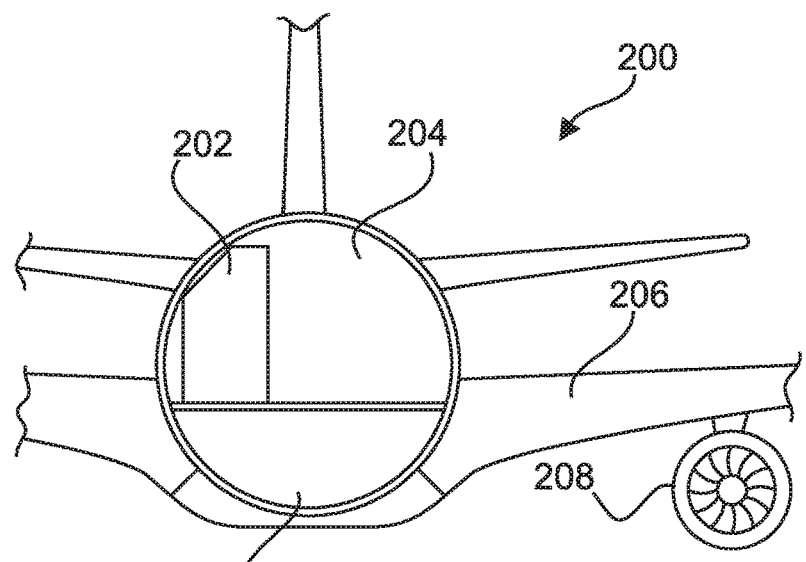
FIG. 8 an example of an aircraft in a longitudinal section.

FIG. 8 shows an example for an aircraft 200, which comprises a fuselage construction 202 and a cabin space 204. In the cabin space 204, exemplarily at least one sanitary module for a vehicle is provided and/or at least one galley module. Additionally, besides the fuselage also wings 206 and engines 208 are provided. A cargo compartment is provided inside of the fuselage construction underneath the cabin.

The cabin space may also be referred to as inner space or as cabin inner space. The cabin space may be designed as a passenger cabin or a crew rest compartment. The term "cabin space" also refers to a cockpit region, after which a sanitary module is provided, e.g. in a cargo aircraft. The term "aircraft" refers to e.g. aeroplanes, helicopters or airships.

As an alternative or additional thereto, e.g. a watercraft, a rail craft or a road craft is provided as the vehicle, e.g. a passenger ship, a train or a bus. The vehicle comprises a body construction and a cabin space. In the cabin space, at least one sanitary module or a galley module according to one of the previous examples is provided, wherein in each case, at least one hand hygiene arrangement is provided. In FIG. 8, the sanitary module is indicated with a rectangle.

Figure 9:
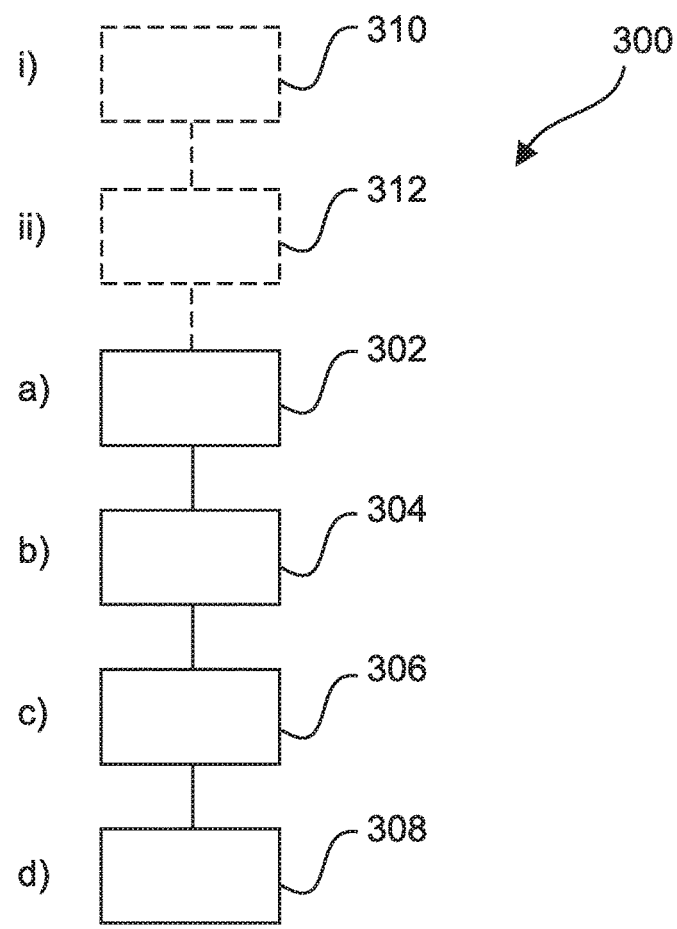
FIG. 9 an example of a method for hand hygiene with optional steps.

In FIG. 9, an example of a method 300 for hand hygiene on board a vehicle is shown. The method 300 comprises the following steps:
- a) In a first step 302, at least one wet hand is arranged in a hand receiving region of a basin device.
- b) In a second step 304, a negative pressure is generated at a disposal opening of the hand receiving region, through which a stream of air in the hand receiving region is generated.
- c) In a third step 306, the hand is dried in the stream of air.
- d) In a fourth step 308, a paper towel thrown into the hand receiving region is discharged through the stream of air. The negative pressure is also used for disposing of water and paper towels via the disposal opening, which forms a common disposal opening.

In FIG. 9 it is indicated with a dashed line as an option that before step a), also further steps may be provided, e.g. in a first step i), i.e. in a first step 310, a water jet is created and at least one hand is arranged in the water jet in order to wash the hand. In a further step 312, also referred to as step ii), a washing of a hand to be dried is conducted. The water is collected and discharged in a collecting region of the basin device. The water collecting region comprises the disposal opening.

The exemplary embodiments described above may be combined in different types and manners. In particular, also aspects of the method may be used for exemplary embodiments of the devices as well as use of the devices and vice versa.

In addition, it should be pointed out that "comprising" does not exclude other elements or steps, and "a" or "an" does not exclude a plural number. Furthermore, it should be pointed out that characteristics or steps which have been described with reference to one of the above exemplary embodiments may also be used in combination with other characteristics or steps of other exemplary embodiments described above. Reference characters in the claims are not to be interpreted as limitations.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A hand hygiene arrangement for the use on board of a vehicle, comprising:
    a washing device;
    a basin device; and
    a drying device;
    wherein the washing device comprises a water supply device for a hand washing process and a spray nozzle;
    wherein the drying device comprises an air discharge device for a hand drying process for generating a stream of air for the hand drying process;
    wherein the arrangement comprises a hand receiving region, wherein the stream of air is generatable in the hand receiving region;
    wherein the air discharge device is connected to the hand receiving region and wherein the arrangement comprises a negative pressure device, which is connected to the air discharge device, wherein the stream of air for the hand drying process is generatable by the negative pressure device;
    wherein the basin device comprises the hand receiving region and a water collecting region comprising a discharge opening in communication with the negative pressure device;
    wherein the discharge opening is configured to permit an unobstructed passage between the basin device and the negative pressure device;
    wherein the spray nozzle is arranged above the basin device and the hand receiving region;
    wherein the air discharge device is connected to the discharge opening of the basin device such that air and fluids are discharged via the discharge opening, which forms a common disposal opening; and
    wherein the negative pressure device is configured for suctioning solids thrown into the water collecting region, besides fluids, for disposal over the common disposal opening.

2. The hand hygiene arrangement according to claim 1, wherein the negative pressure device is configured for suctioning paper towels thrown into the basin device for a disposal over the common disposal opening.

3. The hand hygiene arrangement according to claim 1, wherein downstream of the common disposal opening a separator device for separating solids and fluids is provided.

4. The hand hygiene arrangement according to claim 3, wherein the separator device is a double-walled pipe line,
    wherein an intermediate space is defined between an inner pipe, which is connected to the common disposal opening, and an outer pipe, and wherein the inner pipe comprises a plurality of holes and an inner space created by the inner pipe is connected to the intermediate space through the plurality of holes.

5. The hand hygiene arrangement according to claim 4, wherein the separator device comprises at least one directional change along the flow direction in form of a curvature, in order to exert a centrifugal force on the mixture that flows through, with which fluid contained in the mixture enters the intermediate space through the openings in order to be dischargeable separately.

6. The hand hygiene arrangement according to claim 1, wherein the hand receiving region comprises a hand receiving opening, which is configured as an air supply device, and
wherein a negative pressure is generatable at the negative pressure device, such that ambient air is suctionable and that the stream of air is generatable in the hand receiving region for drying hands.

7. The hand hygiene device according to claim 1, wherein the washing device comprises a water discharge device, and
wherein the discharged water is configured to be conducted through the basin device and the common disposal opening to the water discharge device.

8. The hand hygiene arrangement according to claim 1, wherein the negative pressure device is connected to the common disposal opening to dispose of the collected water and solids and to generate the stream of air.

9. The hand hygiene arrangement according to claim 1, wherein the basin device is has a circumferential water spray device at least partially in an upper edge region of the basin device as a secondary water supply for spraying water from the edge region into the center of the basin device in form of a plurality of spray jets.

10. A sanitary module for a vehicle, the sanitary module comprising:
at least one sanitary function element selected from the group consisting of: toilet, bidet, shower, washbasin and diaper changing table; and
a hand hygiene arrangement comprising:
a washing device;
a basin device; and
a drying device;
wherein the washing device comprises a water supply device for a hand washing process and a spray nozzle,
wherein the drying device comprises an air discharge device for a hand drying process for generating a stream of air for the hand drying process,
wherein the arrangement comprises a hand receiving region, wherein the stream of air is generatable in the hand receiving region,
wherein the air discharge device is connected to the hand receiving region and wherein the arrangement comprises a negative pressure device, which is connected to the air discharge device, wherein the stream of air for the hand drying process is generatable by the negative pressure device,
wherein the basin device comprises the hand receiving region and a water collecting region comprising a discharge opening in communication with the negative pressure device,
wherein the discharge opening is configured to permit an unobstructed passage between the basin device and the negative pressure device;
wherein the spray nozzle is arranged above the basin device and the hand receiving region;
wherein the air discharge device is connected to the discharge opening of the basin device such that air and fluids are discharged via the discharge opening, which forms a common disposal opening, and
wherein the negative pressure device is configured for suctioning solids thrown into the water collecting region, besides fluids, for disposal over the common disposal opening.

11. The sanitary module according to claim 10, wherein the negative pressure device is configured for suctioning paper towels thrown into the basin device for a disposal over the common disposal opening.

12. The sanitary module according to claim 10, wherein downstream of the common disposal opening a separator device for separating solids and fluids is provided.

13. The sanitary module according to claim 12, wherein the separator device is a double-walled pipe line,
wherein an intermediate space is defined between an inner pipe, which is connected to the common disposal opening, and an outer pipe, and
wherein the inner pipe comprises a plurality of holes and an inner space created by the inner pipe is connected to the intermediate space through the plurality of holes.

14. The sanitary module according to claim 13, wherein the separator device comprises at least one directional change along the flow direction in form of a curvature, in order to exert a centrifugal force on the mixture that flows through, with which fluid contained in the mixture enters the intermediate space through the openings in order to be dischargeable separately.

15. The sanitary module according to claim 10, wherein the hand receiving region comprises a hand receiving opening, which is configured as an air supply device, and
wherein a negative pressure is generatable at the negative pressure device, such that ambient air is suctionable and that the stream of air is generatable in the hand receiving region for drying hands.

16. The sanitary module according to claim 10, wherein the washing device comprises a water discharge device, and
wherein the discharged water is configured to be conducted through the basin device and the common disposal opening to the water discharge device.

17. The sanitary module according to claim 10, wherein the negative pressure device is connected to the common disposal opening to dispose of the collected water and solids and to generate the stream of air.

18. The sanitary module according to claim 10, wherein the basin device is has a circumferential water spray device at least partially in an upper edge region of the basin device as a secondary water supply for spraying water from the edge region into the center of the basin device in form of a plurality of spray jets.

\* \* \* \* \*